United States Patent [19]

Dougan et al.

[11] Patent Number: 5,747,293
[45] Date of Patent: May 5, 1998

[54] **INTIMIN-LIKE PROTEINS OF *E. COLI***

[75] Inventors: Gordon Dougan; Gad Frankel, both of London, England

[73] Assignee: Imperial College of Science, Technology & Medicine, London, United Kingdom

[21] Appl. No.: 409,452

[22] Filed: Mar. 23, 1995

[51] Int. Cl.$^6$ ........................ C07K 14/245; C07K 14/00; C07K 14/24
[52] U.S. Cl. ........................ 530/402; 530/350; 530/825
[58] Field of Search .................................... 530/402, 350

[56] References Cited

PUBLICATIONS

Jerse, A., et al., "A genetic locus of enteropathogenic *Escherichia coli* necessary for the production of attaching and effacing lesions on tissue culture cells," *Proc. Natl. Acad. Sci. U.S.A.*, vol. 87, pp. 7839–7843, (Oct. 1990).

Yu, J. and Kaper, J.B., "Cloning and characterization of the eae gene of enterohaemorrhagic *Escherichia coli* O157:H7," *Molecular Microbiology* 6(3), pp. 411–417, (1992).

Frankel, G., et al., "Characterization of the C–Terminal Domains of Intimin–Like Proteins of Enteropathogenic and Enterohemorrhagic *Escherichia coli, Citrobacter freundii,* and *Hafnia alvei*," *Infection and Immunity*, vol. 62, No. 5, pp. 1835–1842, (May 1994).

Donnenberg, M. S., et al., "Role of the eaeA Gene in Experimental Enteropathogenic *Escherichia coli* Infection," *J. Clin. Invest.*, vol 92, pp. 1412–1417, (Sep. 1993).

*Primary Examiner*—Susan A. Loring
*Attorney, Agent, or Firm*—Hale and Dorr LLP

[57] ABSTRACT

The invention is related to antibodies, particularly monoclonal antibodies, which recognize particularly epitopes of the intimin protein of enteropathogenic *E. coli* and enterohemorrhagic *E. coli*, methods of detecting such *E. coli* by use of these antibodies, and kits containing these antibodies for diagnosis.

6 Claims, No Drawings

INTIMIN-LIKE PROTEINS OF E. COLI

The present invention relates to antibodies, particularly monoclonal antibodies which recognise particular epitopes of the intimin protein of enteropathogenic E. coli and enterohemorrhagic E. coli, their use in the detection of such enterophathogenic E. coli, and kits containing such antibody for such use.

Enteropathogenic Escherichia coli (EPEC) were the first E. coli linked with diarrhoea in humans. They are a sub-group of pathogenic E. coli that are a major cause of infant diarrhoea. Enterohemorrhagic E. coli (EHEC) are another such sub-group. EPEC normally fall into several distinct serotype groups based on the type of lipopolysaccharide which is expressed at their cell surface. The most common serogroups that are associated with EPEC are O26, O55, O111, O114, O126, O127, O128, O142 and O157. Although EPEC and EHEC infections are still a serious problem world-wide, no specific treatment or vaccine is as yet available for treating these diseases and furthermore, no relatively simply and/or accurate tests are as yet available for diagnosis.

One major problem in diagnosing EPEC infections is that, apart from the link with several O serotypes, EPEC are difficult to distinguish from commensal, non-pathogenic E. coli which are usually resident in the intestines of healthy individuals. Ultra-structural studies of intestinal biopsy specimens from children with EPEC-induced diarrhoea have shown that EPEC attach to the intestinal epithelium in a characteristic fashion, which is central to the pathogenesis of the disease.

Wherever bacteria bind to the brush border of the intestine, microvilli are destroyed, or "effaced". The apical cell membrane of the bare enterocytes form cup-like pedestals upon which the bacteria intimately adhere. EHEC, Hafnia alvei and Citrobacter freundii biotype 4280 have also been shown to induce similar lesions, termed effacement and attachment lesions, to the intestinal brush border of infected hosts.

Pedestal formation is associated with accumulation of polymerised actin below the surface of the eukaryotic cell directly engulfing the bacteria. This polymerised actin can be detected by staining with a specific dye called phalloidin. A diagnostic test, based on the use of this stain with cultured mammalian cells incubated with pathogenic bacteria has been developed. However, this test is not EPEC-specific, and is expensive and time consuming, which renders its routine use difficult.

The EPEC or EHEC gene product that mediates intimate attachment to epithelial cells is a protein called intimin ($Int_{EPEC}$ and $Int_{EHEC}$ respectively), which is a 94 kdal outer membrane protein encoded by the chromosomal eaeA gene. The amino-terminis of $Int_{EPEC}$ and $Int_{EHEC}$ have a high degree of homology with the eae gene products of Citrobacter freundii biotype 4280 ($Int_{CF}$) and also with the amino terminus of invasin (Inv), the product of inv gene of Yersinia pseudotuberculosis ($Inv_{YP}$) and Yersinia enterocolitica ($Inv_{YE}$).

The DNA and protein sequences of various intimins were disclosed by Kaper (Proc. Natl. Acad. Sci. USA, 87: 7839–7843 (1990) and Mol. Microbiol., 6: 411–417 (1992)).

However, the proteins themselves were not purified. Frankel et al. (Infec. Immun., 62: 1835–1842 (1994)) have isolated the intimin proteins from various sources and have generated Maltose-binding protein (MBP), fusion proteins carrying particular domains of the intimin proteins.

The cell binding activity of $Inv_{YP}$ resides predominantly in the 192 carboxy-terminus amino acids of the protein. Previously, Frankel et al. (supra) used fusions to maltose binding protein (MBP) to show that, like Inv, an Int domain which mediates receptor binding resides in the 280 (or 275 in the case of EHEC) amino acids of the carboxy-terminus of the protein ($Int_{EPEC280}$, $Int_{EHEC275}$, $Int_{HA280}$, $Int_{CF280}$).

However, unlike Inv, which by itself can convert an E. coli K12 strain to an organism capable of attaching and then invading mammalian cells, Int requires the cooperation of other EPEC proteins to induce the effacement and attachment lesion. Notwithstanding that, however, $Int_{EPEC}$ is a virulent factor that induces seroconversion in human volunteers (Donnenberg et al, J. Clin. Invest., 92: 1412–1417 (1993)). The carboxy-terminal domain of this protein is able to bind to target cells and thus it is likely to be surface exposed, thus making it accessible, on whole bacteria, to immune reagents.

We have now generated further fusion proteins in addition to $MEP-Int_{EPEC280}$ (amino acids 660–939). These fusion proteins include different amino acid sequences derived from the 280 binding domain. $MBP-Int_{EPEC150}$ (amino acids 790–939) was found to be the smallest fusion protein that had the ability to mediate cell binding. In addition the cysteine residue at position 937 of Int seems to be required for binding activity, as substitution with serine results in a loss in biological activity. Using the MBP expression system we have obtained high yields of $MBPInt_{EPEC280}$, $MBP-Int_{EHEC275}$, $MBP-Int_{CF280}$ and $MBP-Inv_{YP280}$ fusion proteins. These proteins can be used to immunise mice in order to generate specific monoclonal antibodies. We have now identified monoclonal antibodies which specifically recognise the antigen $MBP-Int_{EPEC280}$ and which do not recognise MBP, $MBP-Int_{EHEC275}$, $MBP-Int_{CF280}$ or $MBP-Inv_{YP280}$. These antibodies are therefore specific for the 280 amino acid domain of $Int_{EPEC}$ and will therefore be useful in both the detection and/or treatment of EPEC infection.

Similarly, $MBP-Int_{EHEC275}$ can be used to generate monoclonal antibodies which recognise $MBP-Int_{EHEC275}$ but not $MBP-Int_{EPEC280}$.

Thus, in a first aspect, the present invention provides an antibody which recognises a region within either the carboxy-terminus 280 amino acid domain of the enteropathogenic E. coli intimin protein ($Int_{EPEC280}$) or the enterohemorrhagic E. coli intimin protein ($Int_{EPEC}280$).

In the context of the present invention, "antibody" refers to conventional polyclonal and monoclonal antibodies and includes antigen binding portions or fragments thereof, e.g. Fab and/or fragments of Fab.

In a preferred embodiment, the antibody is a monoclonal antibody. In particularly preferred embodiments, the antibody is a monoclonal antibody which recognises a region within the following carboxy-terminus 280 amino acid sequence:

| | | | | |
|---|---|---|---|---|
| ITEIKADKTT | AVANGQDAIT | YTVKVMKGDK | PVSNQEVTFT | TTLGKLSNST |
| EKTDTNGYAK | VTLTSTTPGK | SLVSARVSDV | AVDVKAPEVE | FFTTLTDDG |
| NIEIVGTGVK | GKLPTVWLQY | GQVNLKASGG | NGKYTWRSAN | PAIASVDASS |

| | | | | |
|---|---|---|---|---|
| GQVTLKEKGT | TTISVISSDN | QTATYTIATP | NSLIVPNMSK | RVTYNDAVNT |
| CKNFGGKLPS | SQNELENVFK | AWGAANKYEY | YKSSQTIISW | VQQTAQDAKS |
| GVASTYDLVK | QNPLNNIKAS | ESNAYATCVK (SEQ ID NO: 1) | | | or a region within the following carboxy-terminus 275 amino acid sequence:

| | | | | |
|---|---|---|---|---|
| ITEIKADKTT | AVANGKDAIK | YTVKVMKNGQ | PVNNQSVTFS | TNFGMFNGKS |
| QTQATTGNDG | RATTTLTSSS | AGKATVSATV | SDGAEVKATE | VTFFDELKID |
| NKVKIIGNNV | RGELPNIWLQ | YGQFKLKASG | GDGTYSWYSE | NTSIATVDAS |
| GKVTLNGKGS | VVIKATSGDK | QTVSYTIKAP | SYMIKVDKQA | YYADAMSICK |
| NLLPSTQTVL | SKIYDSWGAA | NKYSHYSSMN | SITAWIKQTS | SEQRSGVSST |
| YNLITQNPLP | GVNVNTPNVY | AVCVE (SEQ ID NO: 2). | | |

Preferably, a monoclonal antibody recognising $Int_{EPEC280}$ does not recognise the carboxy-terminus 280 amino acid domain of the intimin protein from enterohemorragic *E. coli* ($Int_{EHEC}275$) or *Citrobacter freundii* biotype 4280 ($Int_{CF}200$) or the carboxy-terminus 280 amino acid domain of the invasion protein from *Yersinia pseudotuberculosis* ($Inv_{YP}200$)

More preferably, the monoclonal antibody recognising $Int_{EPEC280}$ recognises an epitope in the 660–790 amino acid region of the enterophathogenic *E. coli* intimin protein.

Hybridomas producing monoclonal antibodies of the invention are also included within the scope of the invention.

The properties of the monoclonal antibodies of the invention render them useful for detecting enterophathogenic *E. coli* and enterohemorrhagic *E. coli*. Thus, the invention also provides the use of such monoclonal antibodies in detecting enteropathogenic and enterohemorrhagic *E. coli*.

In a further aspect, the invention provides a method for detecting the presence of enteropathogenic or enterohemorrhagic *E. coli* which comprises the step of bringing a sample to be tested into contact with a monoclonal antibody of the invention. In one embodiment, the monoclonal antibody of the invention could be attached to a solid support, for example a test strip or a microtitre well, and the sample containing the antigen could be brought into contact with it.

Suitably, the method will be an ELISA method.

In a further aspect, the invention provides a method for detecting enteropathogenic or enterohemorrhagic *E. coli* infection in a subject which comprises the step of contacting a monoclonal antibody of the invention with a sample obtained from the subject. Suitably, the sample will be a faecal sample.

The fusion proteins (MBP-$Int_{EPEC}280$ and MBP-$Int_{EHEC275}$) are particularly convenient for generating hybridomas capable of producing monoclonal antibodies of the invention, and form another aspect of the present invention.

In a final aspect, the invention provides a peptide having the sequence:

| | | | | | |
|---|---|---|---|---|---|
| a) | ITEIKADKTT | AVANGQDAIT | YTVKVMKGDK | PVSNQEVTFT | TTLGKLSNST |
| | EKTDTNGYAK | VTLTSTTPGK | SLVSARVSDV | AVDVKAPEVE | FFTTLTIDDG |
| | NIEIVGTGVK | GKLPTVWLQY | GQVNLKASGG | NGKYTWRSAN | PAIASVDASS |
| | GQVTLKEKGT | TTISVISSDN | QTATYTIATP | NSLIVPNMSK | RVTYNDAVNT |
| | CKNFGGKLPS | SQNELENVFK | AWGAANKYEY | YKSSQTIISW | VQQTAQDAKS |
| | GVASTYDLVK | QNPLNNIKAS | ESNAYATCVK (SEQ ID NO: 1); or | | |
| b) | ITEIKADKTT | AVANGKDAIK | YTVKVMKNGQ | PVNNQSVTFS | TNFGMFNGKS |
| | QTQATTGNDG | RATTTLTSSS | AGKATVSATV | SDGAEVKATE | VTFFDELKID |
| | NKVKIIGNNV | RGELPNIWLQ | YGQFKLKASG | GDGTYSWYSE | NTSIATVDAS |
| | GKVTLNGKGS | VVIKATSGDK | QTVSYTIKAP | SYMIKVDKQA | YYADAMSICK |
| | NLLPSTQTVL | SKIYDSWGAA | NKYSHYSSMN | SITAWIKQTS | SEQRSGVSST |
| | YNLITQNPLP | GVNVNTPNVY | AVCVE (SEQ ID NO: 2). | | |

The invention will now be described with reference to the following examples which should not be construed as in any way limiting the invention.

EXAMPLE 1

Antibody Production

1. Procedure for Polyclonal Antibodies

50 μg of antigen ($Int_{EPEC280}$) was diluted with 2 ml of PBS. Lyophilised MPL/TDM/CWS adjuvant (Sigma) was reconstituted with the antigen solution. Two rabbits were then immunised and boosted for preparation of polyclonal antibodies as follows:

300 μl were injected intradermally;

400 μl were injected intramuscularly;

100 μl were injected subcutaneously;

200 μl were injected intraperitoneally.

Serum antibodies were tested in an ELISA assay against MBP and MBP-$Int_{EPEC280}$.

EXAMPLE 2

(See also Frankel et al, supra)

(i) Construction of MBP-$Int_{EPEC280}$ and MBP-$Int_{EHEC275}$ Fusion Proteins

Polymerase chain reaction was used to amplify the DNA sequence encoding the carboxy terminus 280 amino acids of Int$_{EPEC}$ (and other MBP-Int$_{EPEC}$ derivatives) and Int$_{EHEC275}$ using EPEC and EHEC chromosomal DNA, respectively, as templates. Forward and reverse primers (including Eco RI and Xba I restriction sites, respectively) were prepared, according to the published DNA sequences, and these were used to amplify both genes. The PCR products (840 bp) were cloned downstream from MalE (encoding MBP) by using the PMAL C2 plasmid.

(ii) Purification of MBP Fusion Proteins

The MBP fusion proteins were purified by amylose chromatography. One liter of Luria broth containing 0.2% glucose and ampicillin was inoculated with 10 ml of an overnight culture of *E. coli* TG1 containing the recombinant pMAL C2 and incubated at 37° C. for 2 h. IPTG was added to final concentration of 0.3 mM and the culture was incubated for an additional 2 h. Subsequent purification was conducted at 4° C. The culture was centrifuged, the supernatant was discarded, the pellet was re-suspended in 30 ml of column buffer (50 mM tris-Hcl pH 7.4, 200 mM NaCl, 1 mM EDTA, 1 mM DTT) and then frozen overnight at −20° C. After thawing and centrifugation, the supernatant was loaded onto an amylose column (20 ml bed volume), previously washed with 200 ml of column buffer. The loaded column was washed with 160 ml of column buffer before the bound material was eluted with column buffer containing 10 mM maltose. Fractions were collected and the optical density at 280 nm was determined. Protein concentration was determined with Bredeford reagent and the purity of the preparation was determined by western blotting using anti-MBP antiserum.

EXAMPLE 3

(i) Preparation of Monoclonal Antibodies

Mice were immunised with the fusion proteins and were boosted last 2–4 days before spleen cells were displaced and lymphocytes were fused with NSO myeloma cells. NSO cells were grown in RPMI 1640 containing 5% FCS and 1% L-Glutamine. Removed spleen were trimmed of any connective tissue and homogenised gently in 5 ml Hanks BSS containing 1 mM HEPES (Hanks/HEPES). The cells were counted and combined with NSO cells that were previously washed with Hanks/HEPES buffer, in a 10:1 ratio (lymphocytes: myelomas). The volume was brought to 50 ml with Hanks/HEPES buffer and the cells were spun at 10000 for 10 min at 25° C. This washing step was repeated twice more. On the last wash, enough supernatant was left to re-suspend the cells in 2 ml of warm DMSO/PEG solution (3 g PEG 1500 in 8.5 ml RPMI 1640, 15% DMSO) was added dropwise over 45 sec. After an additional 20 sec, the PEG was diluted out by adding 10 ml of serum free RPMI dropwise over 60 sec. The volume was brought to 50 ml and the cells were incubated for 5 min before they were pelleted by centrifugation. The pellet was re-suspended in 5 ml of RPMI-20% FCS/HAT (2 ml of 50×stock to 100 ml of RPMI/FCS) and the volume was brought to 90 ml with same medium. 150 ul of the cell suspension were divided into 6×96 well plates. 50 ul medium was added 8 days after the plating.

(ii) Screening for Positive Antibody Secretion

10–14 days after fusion, 50–100 ul of supernatant were removed and tested in an ELISA assay using MBP-Int$_{EPEC}$280 as the coating antigen. Positive supernatants were then tested against MBP using similar assay. Cells secreting MBP-Int$_{EPEC280}$-positive/MBP-negative antibodies were used for cloning.

Details of the ELISA procedure were as follows:

1. Coat wells of Costar EIA plates (Cat. No. 3590) overnight at 4° C. with 50 µl of antigen in PBS (usually 1 µg/ml). If doing capture ELISA, coat overnight with capture agent (antibodies, ganglioside, lectin, etc. diluted in PBS), wash, then add antigen diluted in PBS+0.1% BSA or PBST+0.1% BSA for 1 h at 37° C.
2. Wash 3× with PBST (PBS+0.05% Tween 20).
3. Block 1 hour at 37° C. with 200 µl 1% BSA.
4. Dilute mouse serum in PBST+0.1% BSA. Dilution range 1/50 to 1/50,000.
5. Add 50 µl diluted sera to wells. Incubate 1–2 hours at 37° C.
6. Wash 3× PBST.
7. Add Rabbit anti-mouse HRP conjugate at 1/1000 dilution. 50 µl per well 1–2 hours at 37° C.
8. Wash 3× PBST.
9. Add 50 µl substrate (see below). Incubate at room temperature or 37° C. until colour develops.
10. After 30 min or whenever the reaction is judged to be complete, add 50 µl 12.5% $H_2SO_4$.
11. Read absorbance at 492 nm in plate reader.

Substrate 6.25 ml 0.1M Citric acid (21.01 g/L)

6.15 ml 0.25M $NA_2HPO_4$ 12.5 ml deionised water

Add 10 mg o-phenylene diamine (Sigma tablets)

Add 10 µl 30% $H_2O_2$

NB Can leave antibodies on plate at 4° C. overnight instead.

(iii) Cloning of Specific Hybridomas

Each positive hybridoma was single-cell cloned 3 times and the supernatant tested for the presence of antibodies. At the final cloning step, positive hybridomas were expended and frozen in liquid nitrogen.

EXAMPLE 4

Testing the Monoclonal Antibodies Against Different MBP-Int$_{EPEC}$ Fusion Proteins The repertoire of MBP-Int$_{EPEC}$ fusion proteins was used in an ELISA assay to identify the region within the 280 domain that was recognised by the monoclonal antibodies. MBP, MBP-Int$_{EHEC275}$, MBP-Int$_{CF280}$ and MBP-Inv$_{YP280}$ were used as controls.

RESULTS

Two productive hybridomas secreting specific anti Int$_{EPEC280}$ monoclonal antibodies were cloned. Using an ELISA based assay we found that both monoclonal antibodies reacted with Int$_{EPEC280}$ but not with MBP, MBP-Int$_{EHEC275}$, MBP-Int$_{CF280}$ and MBP-Inv$_{YP280}$. In order to identify the region within the 280 domain that contain the specific epitopes, the monoclonal antibodies were tested against a collection of different MBP-Int$_{EPEC}$ fusion proteins that included in addition to MBP-Int$_{EPEC280}$ (amino acids 660–939) also MBP-Int$_{EPEC150}$ (amino acids 790–939), MBP-Int$_{EPEC120C}$ (amino acids 820–939), MBP-Int$_{EPEC120N}$ (amino acids 790–909), MBP-Int$_{EPEC}$70 (amino acids 870–939); MBP-Int$_{EPEC40}$ (amino acids 820–859) and MBP-Int$_{EPEC280CS}$ (as Int$_{EPEC280}$, but with Cys to Ser substitution at position 937). Both monoclonal antibodies recognised the 280 domain acids domain of Int$_{EPEC}$ but failed to react with any of the other derivatives of Int$_{EPEC}$. We concluded that both monoclonal antibodies recognised an epitope that mapped between amino acids 660–790 of Int. Preliminary results from agglutination assays and ELISA-based tests performed with both monoclonal antibodies, indicated that they can detect expression of intimin at the surface of several serotypes of EPEC but cannot react with eaeA mutant strain of EPEC (CVD206) or with *Citrobacter freundii* biotype 4280.

We claim:

1. A protein which is MBP-Int$_{EPEC280}$ fusion protein.

2. A protein as claimed in claim 1 which comprises the following amino acid sequence:

| | | | | |
|---|---|---|---|---|
| ITEIKADKTT | AVANGQDAIT | YTVKVMKGDK | PVSNQEVTFT | TTLGKLSNST |
| EKTDThGYAK | VTLTSTTPGK | SLVSARVSDV | AVDVKAPEVE | FFTTLTIDDG |
| NIEIVGTGVK | GKLPTVWLQY | GQVNLKASGG | NGKYTWRSAN | PAIASVDASS |
| GQVTLKEKGT | TTISVISSDN | QTATYTIATP | NSLZVPNMSK | RVTYNDAVNT |
| CKNFGGKLPS | SQNELENVFK | AWGAANKYEY | YKSSQTIISW | VQQTAQDAKS |

GVASTYDLVK QNPLNNIKAS ESNAYATCVK (SEQ ID NO: 1).

3. A protein which is MBP-Int$_{EHEC275}$ fusion protein.

4. A protein as claimed in claim 3 which comprises the following amino acid sequence:

| | | | | |
|---|---|---|---|---|
| ITEIKADKTT | AVANGKDAIK | YTVKTMKNGQ | PVNNQSVTFS | TNFGMFNGKS |
| QTQATTGNDG | FATTILTSSS | AGKATVSATV | SDGAEVKATE | VTFFDELKID |
| NKVKIIGNNV | RGELPNIWLQ | YGQFKLKASG | GDGTYSWYSE | NTSIATVDAS |
| GKVTLNGKGS | VVIKATSGDK | QTVSYTIKAP | SYMIKVDKQA | YYADAMSICK |
| NLLPSTQTVL | SKIYDSWGAA | NKYSHYSSMN | SITAWIKQTS | SEQRSGVSST |
| YNLITQNPLP | GVNVNTPNVY | AVCVE (SEQ ID NO: 2). | | |

5. A peptide consisting of the following sequence:

| | | | | |
|---|---|---|---|---|
| ITEIKADKTT | AVANGQDAIT | YTVKVMKGDK | PVSNQEVTFT | TTLGKLSNST |
| EKTDTNGYAK | VTLTSTTPGK | SLVSARVSDV | AVDVKAPEVE | FFTILTIDDG |
| NIEIVGTGVK | GKLPTVWLQY | GQVNLKASGG | NGKYTWRSAN | PAIASVDASS |
| GQVTLKEKGT | TTISVISSDN | QTATYTIATP | NSLIVPNMSK | RVTYNDAVNT |
| CKNFGGKLPS | SQNELENVFK | AWGAANKYEY | YKSSQTIISW | VQQTAQDAKS |
| GAASTYDLVK | QNPLNNIKAS | ESNAYATCVK (SEQ. ID NO: 1). | | |

6. A peptide consisting of the following sequence:

| | | | | |
|---|---|---|---|---|
| ITEIKADKTT | AVANGKDAIK | YTVKVMKNGQ | PVNNQSVTFS | TNFGMFNGKS |
| QTQATTGNDG | RATTILTSSS | AGKATVSATV | SDGAEVKATE | VTFFDELKID |
| NKVKIIGNNV | RGELPNIWLQ | YGQFKLKASG | GDGTYSWYSE | NTSIATVDAS |
| GKVTLNGKGS | VVIKATSGDK | QTVSYTIKAP | SYMIKVDKQA | YYADAMSICK |
| NLLPSTQTVL | SKIYDSWGAA | NKYSHYSSMN | SITAWIKQTS | SEQRSGVSST |
| YNLITQNPLP | GVNVNTPNVY | AVCVE (SEQ. ID NO: 2). | | |

* * * * *

UNITED STATES PATENT AND TRADEMARK OFFICE
CERTIFICATE OF CORRECTION

PATENT NO : 5,747,293
DATED : May 5, 1998
INVENTOR(S) : Gordon DOUGAN and Gad FRANKEL It is certified that error appears in the above-identified patent and that said Letters Patent is hereby corrected as shown below:

In Claim 2, in the amino acid sequence, in the first column, second line, "EKTDThGYAK" should be --EKTDTNGYAK--.

Signed and Sealed this

Seventeenth Day of November, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 280 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Ile Thr Glu Ile Lys Ala Asp Lys Thr Thr Ala Val Ala Asn Gly Gln
 1               5                  10                  15
Asp Ala Ile Thr Tyr Thr Val Lys Val Met Lys Gly Asp Lys Pro Val
             20                  25                  30
Ser Asn Gln Glu Val Thr Phe Thr Thr Thr Leu Gly Lys Leu Ser Asn
         35                  40                  45
Ser Thr Glu Lys Thr Asp Thr Asn Gly Tyr Ala Lys Val Thr Leu Thr
     50                  55                  60
Ser Thr Thr Pro Gly Lys Ser Leu Val Ser Ala Arg Val Ser Asp Val
 65                  70                  75                  80
Ala Val Asp Val Lys Ala Pro Glu Val Glu Phe Phe Thr Thr Leu Thr
                 85                  90                  95
Ile Asp Asp Gly Asn Ile Glu Ile Val Gly Thr Gly Val Lys Gly Lys
             100                 105                 110
Leu Pro Thr Val Trp Leu Gln Tyr Gly Gln Val Asn Leu Lys Ala Ser
         115                 120                 125
Gly Gly Asn Gly Lys Tyr Thr Trp Arg Ser Ala Asn Pro Ala Ile Ala
     130                 135                 140
Ser Val Asp Ala Ser Ser Gly Gln Val Thr Leu Lys Glu Lys Gly Thr
145                 150                 155                 160
Thr Thr Ile Ser Val Ile Ser Ser Asp Asn Gln Thr Ala Thr Tyr Thr
                 165                 170                 175
Ile Ala Thr Pro Asn Ser Leu Ile Val Pro Asn Met Ser Lys Arg Val
             180                 185                 190
Thr Tyr Asn Asp Ala Val Asn Thr Cys Lys Asn Phe Gly Gly Lys Leu
         195                 200                 205
Pro Ser Ser Gln Asn Glu Leu Glu Asn Val Phe Lys Ala Trp Gly Ala
     210                 215                 220
Ala Asn Lys Tyr Glu Tyr Tyr Lys Ser Ser Gln Thr Ile Ile Ser Trp
225                 230                 235                 240
Val Gln Gln Thr Ala Gln Asp Ala Lys Ser Gly Val Ala Ser Thr Tyr
                 245                 250                 255
Asp Leu Val Lys Gln Asn Pro Leu Asn Asn Ile Lys Ala Ser Glu Ser
             260                 265                 270
Asn Ala Tyr Ala Thr Cys Val Lys
         275                 280
```

( 2 ) INFORMATION FOR SEQ ID NO: 2:

( i ) SEQUENCE CHARACTERISTICS:
        ( A ) LENGTH: 275 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

```
Ile Thr Glu Ile Lys Ala Asp Lys Thr Thr Ala Val Ala Asn Gly Lys
 1           5                  10                 15

Asp Ala Ile Lys Tyr Thr Val Lys Val Met Lys Asn Gly Gln Pro Val
            20                 25                 30

Asn Asn Gln Ser Val Thr Phe Ser Thr Asn Phe Gly Met Phe Asn Gly
         35                 40                 45

Lys Ser Gln Thr Gln Ala Thr Thr Gly Asn Asp Gly Arg Ala Thr Ile
 50                     55                 60

Thr Leu Thr Ser Ser Ser Ala Gly Lys Ala Thr Val Ser Ala Thr Val
 65                  70                 75                 80

Ser Asp Gly Ala Glu Val Lys Ala Thr Glu Val Thr Phe Phe Asp Glu
                 85                 90                 95

Leu Lys Ile Asp Asn Lys Val Lys Ile Ile Gly Asn Asn Val Arg Gly
             100                105                110

Glu Leu Pro Asn Ile Trp Leu Gln Tyr Gly Gln Phe Lys Leu Lys Ala
         115                120                125

Ser Gly Gly Asp Gly Thr Tyr Ser Trp Tyr Ser Glu Asn Thr Ser Ile
     130                135                140

Ala Thr Val Asp Ala Ser Gly Lys Val Thr Leu Asn Gly Lys Gly Ser
145                150                155                160

Val Val Ile Lys Ala Thr Ser Gly Asp Lys Gln Thr Val Ser Tyr Thr
                 165                170                175

Ile Lys Ala Pro Ser Tyr Met Ile Lys Val Asp Lys Gln Ala Tyr Tyr
             180                185                190

Ala Asp Ala Met Ser Ile Cys Lys Asn Leu Leu Pro Ser Thr Gln Thr
         195                200                205

Val Leu Ser Lys Ile Tyr Asp Ser Trp Gly Ala Ala Asn Lys Tyr Ser
     210                215                220

His Tyr Ser Ser Met Asn Ser Ile Thr Ala Trp Ile Lys Gln Thr Ser
225                230                235                240

Ser Glu Gln Arg Ser Gly Val Ser Ser Thr Tyr Asn Leu Ile Thr Gln
                 245                250                255

Asn Pro Leu Pro Gly Val Asn Val Asn Thr Pro Asn Val Tyr Ala Val
             260                265                270

Cys Val Glu
        275
```